United States Patent [19]

Arai et al.

[11] Patent Number: 4,721,584

[45] Date of Patent: Jan. 26, 1988

[54] METHOD OF CONCENTRATION AND SEPARATION OF UNSATURATED FATTY ACID ESTERS

[75] Inventors: Makoto Arai; Hideki Fukuda, both of Takasago, Japan

[73] Assignee: Kanegafuchi Kagaku Kogyo Kabushiki Kaisha, Osaka, Japan

[21] Appl. No.: 931,100

[22] Filed: Nov. 17, 1986

[30] Foreign Application Priority Data

Nov. 21, 1985 [JP] Japan .................................. 60-262262
Apr. 2, 1986 [JP] Japan .................................. 61-76062
Aug. 22, 1986 [JP] Japan .................................. 61-197884

[51] Int. Cl.$^4$ .............................................. C11C 1/08
[52] U.S. Cl. ................................................... 260/428.5
[58] Field of Search ............................... 260/428.5, 428

[56] References Cited

U.S. PATENT DOCUMENTS

| | | | |
|---|---|---|---|
| 4,048,205 | 9/1977 | Neuzil et al. | 260/428.5 |
| 4,049,688 | 9/1977 | Neuzil et al. | 260/428.5 |
| 4,066,677 | 1/1978 | de Rosset et al. | 260/428.5 |
| 4,210,594 | 7/1980 | Logan et al. | 260/428.5 |
| 4,213,913 | 7/1980 | de Rosset | 260/428.5 |
| 4,305,882 | 12/1981 | Emken et al. | 260/428.5 |

FOREIGN PATENT DOCUMENTS

| | | |
|---|---|---|
| 0001854 | 5/1979 | European Pat. Off. . |
| 0002545 | 6/1979 | European Pat. Off. . |
| 1240513 | 7/1971 | United Kingdom . |

*Primary Examiner*—J. E. Evans
*Attorney, Agent, or Firm*—Armstrong, Nikaido, Marmelstein & Kubovcik

[57] ABSTRACT

This invention provides a method of concentrating and separating γ-linolenic acid esters and/or arachidonic acid esters characterized in that a fatty acid ester mixture containing γ-linolenic acid ester and/or arachidonic acid ester is brought in contact with crystalline aluminosilicate zeolites to make adsorption and desorption. According to this invention, high purity γ-linolenic acid and/or arachidonic acid ester(s) may be obtained on industrial scale.

20 Claims, No Drawings

METHOD OF CONCENTRATION AND SEPARATION OF UNSATURATED FATTY ACID ESTERS

BACKGROUND OF THE INVENTION

1. Field of the Invention

The present invention relates to a method of concentration and separation of $\gamma$-linolenic acid esters or arachidonic acid esters by taking advantage of the difference in affinity of highly unsaturated fatty acid esters to zeolites.

2. Description of the Prior Art $\gamma$-Linolenic acid (hereinafter abbreviated to GLA) and arachidonic acid (hereinafter abbreviated to AA) are important materials as precursory materials to prostaglandin and are recently drawing particular attention because of their divergent physiological activities. Particularly, as a result of discovery that GLA or AA can be mass-produced utilizing various species of microorganisms, active research and development have been pursued on them.

Heretofore known as general methods for concentration and separation of GLA and AA from mixtures of fatty acid esters are urea adduct process and silver complex process (both covered by British Pat. No. 1240513); by the former method, the products' purities are low and the urea's cost is high and the latter method also involves high cost of silver; therefore, they both can hardly be said suitable for application on industrial scale. As other potentially effective methods, enzyme method, low temperature fractional crystallization method, supercritical fluid extraction method, molecular distillation method, etc., may be mentioned. With these methods, many defects and technical themes to resolve in the aspects of purity, cost and operation are left and therefore, it is quite difficult to obtain GLA and AA at high purity on industrial scale.

SUMMARY OF THE INVENTION

The object of this invention is to provide a method of concentration and separation of unsaturated fatty acid esters for obtaining GLA and/or AA at high purity on industrial scale.

Other objects and advantages of this invention will become apparent from the following detailed description of this invention.

The present inventors, as a result of their assiduous study in an effort to attain the aforementioned objective, have discovered that the desired high purity GLA esters and AA esters can be readily obtained by making adsorption-desorption operation, using crystalline aluminosilicate zeolites, which has led to completion of this invention.

DETAILED DESCRIPTION OF THE INVENTION

The present invention relates to a method of concentration and separation of $\gamma$-linolenic acid esters and/or arachidonic acid esters characterized in that a mixture of fatty acid esters containing $\gamma$-linolenic acid ester and/or arachidonic acid ester is brought in contact with crystalline aluminosilicate zeolites, to be adsorbed thereby and then, desorbed therefrom.

The concentration and separation method of this invention comprises more particularly (1) a process of dissolving in a nonpolar solvent a fatty acid ester mixture containing GLA ester or AA ester and bringing this solution in contact with crystalline aluminosilicate zeolites, thereby selectively adsorbing the GLA ester and the AA ester, then (2) desorbing the GLA ester and the AA ester by contacting the aforementioned crystalline aluminosilicate zeolites with a polar solvent and finally, (3) a process of removing the polar solvent from the GLA ester or AA ester containing solution.

The fatty acid esters used according to this invention include esters obtained from lipid containing GLA or AA or both and such lower alcohols as methanol, ethanol, propanol, butanol, etc., and in addition, fatty acid esters of such polyvalent alcohols as glycol, glycerine, etc. Lipid containing GLA and AA may be produced, for example, by such genera of molds as Aspergillus, Fusarium, Penicillium, Mucor, Rhizopus, Mortierella, Cunninghamella, Choanephora, etc., or such genera of algae as Spirulina, Porphyridium, etc., seeds of evening primrose or fish oils, etc. Such lipid is turned into fatty acid esters by undergoing ester exchange with one of the aforementioned alcohols in the presence of an appropriate catalyzer.

As the crystalline aluminosilicate zeolites, any arbitrary ones which contain both silica and alumina are usable, but particularly, those with mol ratio of $SiO_2/Al_2O_3$ not less than 3 are preferable from the standpoint of selectivity and rate of adsorption of GLA esters and AA esters. As zeolites which meet these conditions, those available on the market such as Y-type zeolites, mordenite, erionite, ferrielite, L-type zeolites, etc., are usable, but use of crystalline aluminosilicate zeolites which are subjected to such treatments as ion exchange, etc., will result in great improvement in the ability of concentration and separation, depending on the fatty acid composition (or the type of alcohol which is combined with fatty acids as esters) in the fatty acid ester mixture. As the cations which improve the ability of concentration and separation through ion exchange, for example, $K^+$, $Na^+$, $Ag^+$, $Cs^+$, $Rb^{30}$, $Li^+$, $Mn^{2+}$, $Cu^{2+}$, $Ca^{2+}$, $Mg^{2+}$, $Ba^{2+}$, $Be^{2+}$, $Sr^{2+}$, $Fe^{3+}$, $La^{3+}$, $Ce^{3+}$, $Sc^{3+}$, $Y^{3+}$, $NH_4^+$, $CH_3NH_3^+$, $(CH_3)_2NH_2^+$, $C_2H_5NH_3^+$, etc., may be mentioned. These cations are of course effective not only singly but in the state of two or more members coexisting. In this instance, replacing sodium with any of the aforementioned cations until it is reduced to 5.0% by weight or less in the crystal thus produced should be preferable from the standpoint of selectivity and rate of adsorption. Particularly, when separating GLA esters from a mixture of fatty acid ethyl esters or methyl esters, use of Y-type zeolite being sodium Y-type zeolite available on the market which has been subjected to ion exchange with cation(s) including $K^+$, $Rb^+$, $Cs^+$, $NH_4^+$, $CH_3NH_3^+$, $(CH_3)_2NH_2^+$ and $C_2H_5NH_3^+$ is very effective from the standpoint of selectivity of GLA esters. The ion exchange of zeolite available on the market may be readily made by a normally well-known method; thus, the specified zeolite is dipped in an aqueous solution of salts containing the cation(s) with which the exchange is desired to be made, e.g., $K^+$, $Rb^+$, $Cs^+$, $Ag^+$, $Cu^{2+}$, $Mn^{2+}$, $Mg^{2+}$, $Ba^{2+}$, $Fe^{3+}$, $NH_4^+$ or $CH_3NH_3^+$, etc., and this solution is held at 70°–100° C. and stirred for about 24 hr; this operation is repeated several times; after this treatment, the zeolites are dried in atomosphere at 120°–700° C. or calcined; in this way ion exchanged zeolites are readily obtained. However, heat treatment at high temperatures of $NH_4^+$, $CH_3NH_3^+$, $(CH_3)_2NH_2^+$ and $C_2H_5NH_3^+$ of removal of ammonia or inducement of chemical reactions; therefore, the drying temperature range should preferably be on the order of 120° C.–250° C. to have any of these cations contained in zeolites.

The zeolites used may have whatever form, powders, pellets, beads, granules, etc. As zeolites with the mole ratio of $SiO_2/Al_2O_3$ lower than 3, for example, X-type and A-type which are normally available on the market may be mentioned, but they are substantially inferior to the aforementioned zeolites in selectivity and rate of adsorption of GLA esters and AA esters; therefore, they are hardly applicable.

As the nonpolar solvents used according to this invention, straight chain or cyclic nonpolar solvents such as n-heptane, n-hexane, cyclohexane, benzene, p-xylene, n-octane, etc., may be utilized; of course, mixed solvents of two or more members of them are usable. As the polar solvents for desorption, wide range of polar solvents such as acetone, methanol, ethanol, chloroform, diethyl ether, ethyl acetate, etc., may be used. And two or more members of these polar solvents in mixture or those prepared by mixing polar solvents and nonpolar solvents to alter the polarity of the polar solvents may be employed.

When obtaining high purity GLA esters or AA esters by the later-described column operation method, as the polar solvent used in desorbing fatty acid esters, the aforementioned polar solvents may be used singly, but use of solvents having any of the aforementioned polar solvents mixed with nonpolar solvents at 0.01%–10% by volume in proportion thereto should be preferable because it is capable of separting the fatty acid esters desorbed more finely, which enhances the GLA esters or AA esters. When, for example, n-hexane containing 20% ethanol is used as the polar solvent for desorption, the purities of the GLA esters obtained are 70% at the most, but with use of n-hexane containing 0.1% ethanol, GLA esters with purities 90% or higher may be readily obtained.

The temperature when fatty acid esters and various solvents are brought in contact with zeolites should normally be on the order of the temperature range (10° C.–90° C.) which is used for adsorption operation of solvents. If the temperature is too low, impurities other than GLA esters and AA esters will be adsorbed in large amounts; this is undesirable. On the other hand, at too high temperatures, unsaturated fatty acids tend to be denatured and if the temperatures are higher than the boiling point of the solvent used, the operation must be performed under pressure, to economic disadvantage. A particularly desirable operation temperature range is 20° C.–50° C.

In the adsorption process of this invention, a fatty acid ester mixture containing GLA ester and AA ester is dissolved in a nonpolar solvent which is 30 times or less in weight ratio thereto. (1) This solution is put in a stirring tank; then, with crystalline aluminosilicate zeolites added 0.05–5 times said fatty acid ester mixture in weight ratio thereto, the solution is stirred for 0.5–10 hr, thereby making selective adsorption of GLA ester and AA ester. (2) Said fatty acid ester mixture solution is passed through zeolites prefilled in a column in contact therewith, thereby making selective adsorption of GLA ester and AA ester. These methods are applicable. With regard to the amount of the solution passed in the column operation of (2), normally, the operation may be run with the liquid hourly space velocity (LHSV) in the range of 0.5–10, similarly as in the operation with silica gel or ion exchange resin. Or by setting the column operation pressure above atmospheric pressure, e.g., from the intermediate pressures of 10–100 kg/cm² to high pressures, this column may be utilized as a compacter separation column. Particularly, when high purity GLA esters or AA esters are desired to have, the column operation is preferred.

Then in the desorption process, when the aforementioned (1) is applied, after filtering and fractionating the nonpolar solvent inside the tank, a polar solvent is added 0.5–30 times the crystalline aluminosilicate zeolites in weight ratio thereto and the mixed solution is stirred for 0.5–5 hr; by repeating this treatment about 2–5 times, GLA ester and AA ester may be concentrated and separated. And when the aforementioned (2) is applied, GLA ester and AA ester may be desorbed by passing a polar solvent through the crystalline aluminosilicate zeolites column under the condition of a liquid hourly space velocity (LHSV) being 0.05–10. In this instance, a polar solvent 10–100 times the crystalline aluminosilicate zeolites in weight ratio thereto is passed and the solution flowing out from the column is divided into 2–100 fractions, whereby the fatty acid esters may be successively desorbed in the order of increasing affinity to the zeolites, to be separated simultaneously. And if the polar solvent used is not merely one type, but those of various types are used and those with gradually increasing polarities are passed, various types of fatty acid esters may be divided into fraction at high efficiency.

Finally, the polar solvent is removed by distilling the fraction with high concentration of GLA ester or AA ester in the divided solution, whereby it is possible to obtain high purity GLA ester and AA ester. Fractions of other fatty acid esters may be similarly recovered. The crystalline aluminosilicate zeolites, after having been fractionated, are washed with a nonpolar solvent; then, such gas as nitrogen, etc., is passed therethrough, followed by drying at 100°–500° C., and so forth. This operation enables its repetitive use.

The GLA and AA obtained by the aforementioned operation have very high purity; the separation method is highly advantageous in cost, as compared with conventional methods, and promises enormous contribution in planning its industrialization.

In the following, this invention is described particularly in connection with its preferred embodiments, but it will not be bound thereby. In these examples, percentage (%) means % by weight, unless otherwise specified.

EXAMPLE 1

A 1N aqueous solution of each of various was put in a flask in proportion of 100 ml to 5 g of sodium Y type zeolite (trade name SK-40) with $SiO_2/Al_2O_3$ mol ratio approx. 5 manufactured by Union Carbide Corp.; the system was stirred at temperatures of 90°–100° C. for 24 hr, thereby exchanging sodium ions with the other ion(s), followed by water rinsing, and then, the product was dried at 160° C. for 1 hr. In this instance, the sodium content in zeolites was set always 5.0% by weight or less.

On the other hand, Mucor ambiguus IFO 6472 was subjected to aerobic cultivation at 30° C. for approx. 70 hr in a culture of 4% glucose, 0.3% $KH_2PO_4$, 0.2% $(NH_4)_2SO_4$, 0.1% $(NH_2)_2CO$, 0.05% $MgSO_4.7H_2O$, 0.001% $FeSO_4.7H_2O$, 0.001% $CaCl_2.2H_2O$, 0.00002% $CuSO_4.5H_2O$, 0.0001% $ZnSO_4.7H_2O$, 0.0001% $MnCl_2.4H_2O$, 0.01% NaCl, 0.04% yeast essence, 0.04% malt essence and 0.02% polypeptone, and then, the lipid accumulated in this fungus was extracted by homogenization. The lipid obtained in this way was subjected to ester exchange in 0.5N NaOH methanol solution, yielding a methyl ester mixture of the fatty acid composition shown in Table 1.

In Table 1, $C_{n:k}$ represents fatty acid esters defined by the molecular formula $C_{n-1}H_{2(n-k)-1}COOR$ (R: alkyl group). The same applies hereinafter.

Five grams of this fatty acid ester mixture was dissolved by addition of 30 g of n-heptane; to this solution 2.5 g of each of various Y type zeolites prepared as hereabove-described was added and this system was stirred at 25° C. for 1 hr, followed by filtration. Thereafter, 30 g of chloroform was added to this zeolite, the system was then, stirred at 25° C. for 2 hr, followed by filtration, and the filtrate was condensed. The amounts (g) of the total fatty acid esters thus obtained and the fatty acid compositions are shown in Table 2.

Jointly listed in Table 2 are results of experiments conducted at the same time by the similar method as hereabove-described using sodium Y type zeolite (trade name SK-40) available on the market, hydrogen Y type zeolite with $SiO_2/Al_2O_3$ mol ratio approx. 5.5 (trade name TSZ-303PSH2, manufactured by Toyo Soda Co.), sodium mordenite with $SiO_2/Al_2O_3$ mol ratio ratio approx. 10 (trade name Zeolon 900Na, manufactured by Norton Corp.), sodium X type zeolite with $SiO_2/Al_2O_3$ mol ratio approx. 2.5 (trade name Molecular Sieves 13X, manufactured by Union Carbide Corp.)

Table 2 implies that use of zeolite with $SiO_2/Al_2O_3$ mol ratio 3 or higher will greatly improve the purity of the GLA esters.

TABLE 1

| Component | C 16:0 | C 16:1 | C 18:0 | C 18:1 | C 18:2 | C 18:3 (GLA) | Others |
|---|---|---|---|---|---|---|---|
| Composition (%) | 11.0 | 8.5 | 1.6 | 36.9 | 22.5 | 15.7 | 3.8 |

TABLE 2

| Adsorbent | $SiO_2/Al_2O_3$ mol ratio (—) | Oil amount (g) | C 16:0 | C 16:1 | C 18:0 (%) | C 18:1 | C 18:2 | C 18:3 (GLA) | Others |
|---|---|---|---|---|---|---|---|---|---|
| Potassium Y | 4.8 | 0.78 | 1.8 | 9.3 | 0 | 5.1 | 12.2 | 70.5 | 1.1 |
| Copper Y | 4.8 | 0.64 | 2.3 | 8.8 | 0.1 | 9.2 | 10.8 | 67.4 | 1.4 |
| Manganese Y | 4.8 | 0.61 | 3.2 | 12.2 | 0.3 | 11.6 | 13.4 | 58.2 | 1.1 |
| Iron Y | 4.8 | 0.72 | 1.6 | 10.7 | 0.1 | 8.5 | 11.9 | 64.6 | 2.6 |
| Silver Y | 4.8 | 0.68 | 0.2 | 11.3 | 0.1 | 6.8 | 13.2 | 66.3 | 2.1 |
| Cesium Y | 4.8 | 0.58 | 0.5 | 8.7 | 0.4 | 10.8 | 11.9 | 66.3 | 1.4 |
| Rubidium Y | 4.8 | 0.62 | 0.1 | 7.3 | 0.1 | 9.4 | 12.2 | 69.8 | 1.1 |
| Ammonium Y | 4.8 | 0.70 | 2.5 | 10.4 | 0.6 | 8.5 | 11.8 | 65.3 | 0.9 |
| Methyl ammonium Y | 4.8 | 0.54 | 3.3 | 8.8 | 0.3 | 10.0 | 12.3 | 64.0 | 1.3 |
| Sodium Y type | 4.8 | 0.61 | 1.8 | 15.2 | 0.6 | 15.5 | 15.6 | 48.2 | 3.1 |
| Sodium mordenite | 9.8 | 0.66 | 1.8 | 10.3 | 0.5 | 9.9 | 16.9 | 60.1 | 0.5 |
| Hydrogen Y type | 5.5 | 0.53 | 3.5 | 14.2 | 0.3 | 21.6 | 18.1 | 40.6 | 1.7 |
| Sodium X type | 2.5 | 0.53 | 2.5 | 13.8 | 0.8 | 29.1 | 23.3 | 29.2 | 1.3 |
| 5A type | 1.9 | 0.08 | 9.6 | 18.4 | 0.6 | 28.3 | 17.2 | 21.1 | 4.8 |

EXAMPLE 2

Various Y type zeolites were prepared through ion exchange with various cations by the similar method as in Example 1 using sodium Y type zeolite with $SiO_2/Al_2O_3$ mol ratio 5.3 (trade name TSZ-320 NAD) manufactured by Toyo Soda Company. The same fatty acid ester mixture as used in Example 1 was concentrated by the same operation of adsorption-desorption as in Example 1, using various Y type zeolites. The results are shown in Table 3. In this table, the "ion exchange rate" represents the percentage of $Na^+$ contained in the zeolite available on the market which has been exchanged by any of other cations.

TABLE 3

| Adsorbent | $SiO_2/Al_2O_3$ mol ratio (—) | Ion exchange rate (%) | Oil amount (g) | C 16:0 | C 16:1 | C 18:0 (%) | C 18:1 | C 18:2 | C 18:3 (GLA) | Others |
|---|---|---|---|---|---|---|---|---|---|---|
| Potassium Y | 5.3 | 82.5 | 0.87 | 0.4 | 10.0 | 0.2 | 4.9 | 11.8 | 72.3 | 0.4 |
| Copper Y | 5.3 | 74.3 | 0.75 | 3.2 | 9.8 | 0.8 | 3.8 | 12.3 | 69.9 | 0.2 |
| Silver Y | 5.3 | 72.1 | 0.79 | 1.3 | 10.1 | 0.6 | 5.0 | 10.5 | 72.0 | 0.5 |
| Cesium Y | 5.3 | 58.3 | 0.68 | 2.3 | 8.9 | 0.1 | 5.8 | 12.9 | 69.3 | 0.7 |
| Rubidium Y | 5.3 | 66.3 | 0.69 | 1.9 | 9.8 | 0.2 | 4.2 | 13.5 | 69.0 | 1.4 |
| Ammonium Y | 5.3 | 93.0 | 0.65 | 3.3 | 6.9 | 0.3 | 6.6 | 12.3 | 68.9 | 1.7 |
| Methyl ammonium Y | 5.3 | 74.9 | 0.59 | 2.1 | 9.9 | 0.1 | 5.8 | 12.6 | 69.1 | 0.4 |
| Sodium Y type | 5.3 | — | 0.60 | 3.3 | 11.0 | 1.6 | 8.3 | 16.6 | 58.3 | 0.9 |
| Sodium X type | 2.5 | — | 0.45 | 2.0 | 14.5 | 0.6 | 28.3 | 24.2 | 30.1 | 0.3 |
| 5A type | 1.9 | — | 0.33 | 0.4 | 13.9 | 0.2 | 42.0 | 23.3 | 19.8 | 0.4 |

EXAMPLE 3

Five grams of fatty acid methyl ester mixture, the same material as of Example 1, was dissolved in 6 g of n-heptane and this solution was passed through a glass column 2.1 cm in ID and 50 cm long filled with 50 g of potassium Y type zeolite prepared similarly as in Example 1. The polarity of the elution solvent was raised little by little from that of 100% n-heptane by successively mixing increasing amounts of chloroform. The column was held at a temperature of 40° C. under normal pressure and the elution was conducted at a liquid hourly space velocity of elution solvent of 1.0 (1/hr). The eluate was divided into 10 ml fractions. The types and amounts of the elution solvents used are given hereunder.

| 1 | Fraction Nos. 1–30 | 300 ml |
|---|---|---|
|   | n-Heptane | |
| 2 | Fraction Nos. 31–50 | 200 ml |
|   | n-Heptane:Chloroform = 4:1 | |
| 3 | Fraction Nos. 51–70 | 200 ml |
|   | n-Heptane:Chloroform = 5:5 | |
| 4 | Fraction Nos. 71–100 | 300 ml |
|   | n-Heptane:Chloroform = 1:3 | |

By removing by way of distillation the elution solvent of Fraction Nos. 60–64 obtained in this way, 0.20 g of fatty acid methyl ester was obtained. The fatty acid composition of the fatty acid esters is shown in Table 4. It indicates that the purity of γ-linolenic acid ester is remarkably upgraded.

TABLE 4

| Adsorbent | $SiO_2/Al_2O_3$ mol ratio (—) | Oil amount (g) | C 16:0 | C 16:1 | C 18:0 | C 18:1 | C 18:2 | C 18:3 (GLA) | Others |
|---|---|---|---|---|---|---|---|---|---|
| Potassium Y | 4.8 | 0.20 | 0.4 | 3.8 | 0.2 | 3.3 | 3.0 | 85.5 | 3.8 |

EXAMPLE 4

Five grams of methyl ester mixture of the same fatty acid composition as of Example 1 was dissolved in 6 g of n-hexane and this solution was passed through a glass column 2.1 cm in ID and 50 cm long which was filled with 50 g of potassium Y type zeolite prepared similarly as in Example 2. With regard to the elution solvents, first 900 ml of n-hexane only was passed; then, 2100 ml of a solution of n-hexane mixed with 0.1% by volume of ethanol was passed. The elution was conducted while holding the column at a temperature of 30° C. under normal pressure and at liquid hourly space velocity of the elution solvent of 1.0 (1/hr) and the eluate was divided into 50 ml fractions.

By removing by way of distillation the elution solvent of Fraction Nos. 71–74 obtained in this way, 0.18 g of fatty acid methyl ester was obtained. The fatty acid composition of this fatty acid esters is shown in Table 5. It indicates that the purity of GLA ester is remarkably upgraded. On the other hand, when a solution of n-hexane mixed with 20% by volume of ethanol was used as the elution solvent, the purity of GLA ester was 70.5%.

TABLE 5

| Adsorbent | $SiO_2/Al_2O_3$ mol ratio (—) | Oil amount (g) | C 16:0 | C 16:1 | C 18:0 (%) | C 18:1 | C 18:2 | C 18:3 (GLA) | Others |
|---|---|---|---|---|---|---|---|---|---|
| Potassium Y | 5.3 | 0.18 | 0.4 | 1.8 | 0.2 | 0.3 | 3.0 | 92.5 | 1.8 |

EXAMPLE 5

An alga porphyridium cruentum was planted in a culture consisting of 2.7% NaCl, 0.1% $KNO_3$, 0.007% $KH_2PO_4$, 0.004% $NaHCO_3$, 0.66% $MgSO_4.7H_2O$, 0.56% $MgCl_2.6H_2O$, 0.15% $CaCl_2.2H_2O$, $4\times10^{-6}\%$ $ZnCl_2$, $6\times10^{-5}\%$ $H_3BO_4$, $1.5\times10^{-5}\%$ $CoCl_2.6H_2O$, $4\times10^{-6}\%$ $CuCl_2.2H_2O$, $4\times10^{-5}\%$ $MnCl_2.4H_2O$, $3.7\times10^{-5}\%$ Mo, 1 ml/l of $FeCl_2.4H_2O$ (240 mg/100 ml 0.05 M $Na_2$ EDTA) and 20 ml/l of 1M Tris-HCl solution (pH 7.6) and cultivated at a temperature of 23° C. and under exposure to approx. 8,000 lx illuminance fluorescent light, while passing carbon dioxide gas through the culture. The composition of the lipid obtained in this way which was then, turned into fatty acid methyl esters is shown in Table 6.

TABLE 6

| Component | C 16:0 | C + C 18:0 | C 18:1 | C 20:4 (AA) | Others |
|---|---|---|---|---|---|
| Composition | 35.1 | 12.6 | | 49.8 | 2.5 |

(%)

Five grams of this fatty acid methyl ester mixture was dissolved in 6 g n-hexane; with this solution, the same operation as of Example 4 was run and then, by removing the elution solvent of Fraction Nos. 86–90 by way of distillation, 2.3 g of fatty acid methyl esters were obtained. The fatty acid composition of this fatty acid esters is shown in Table 7. It suggests that the purity of AA ester is drastically improved.

TABLE 7

| Adsorbent | Oil amount (g) | C 16:0 | C 18:0 | C 18:1 | C 20:4 (AA) | Others |
|---|---|---|---|---|---|---|
| Potassium Y | 2.3 | 0 | | 0.5 | 98.3 | 1.2 |

EXAMPLE 6

Results obtained by the same operation with the same materials as in Example 1, using various solvents in place of the nonpolar solvent n-heptane and the polar solvent chloroform, are shown in Table 8. The zeolite used was potassium Y type zeolite obtained by the same method as of Example 1.

Results of Table 8 clearly veryfy that in every case, the purity was remarkably improved.

TABLE 8

| Nonpolar solvent for dissolving ester mixtures | Polar solvents for elution | Oil amount (g) | C 16:0 | C 16:1 | C 18:0 (%) | C 18:1 | C 18:2 | C 18:3 (GLA) | Others |
|---|---|---|---|---|---|---|---|---|---|
| n-Heptane (30 g) | Chloroform (30 g) | 0.78 | 1.8 | 9.3 | 0 | 5.1 | 12.2 | 70.5 | 1.1 |
| n-Hexane (30 g) | Chloroform (30 g) | 0.60 | 0.9 | 9.2 | 0.2 | 7.9 | 15.1 | 65.7 | 1.0 |
| Cyclohexane (50 g) | Ethanol (30 g) | 0.58 | 0.8 | 11.0 | 0.4 | 8.2 | 16.3 | 61.0 | 2.3 |

TABLE 8-continued

| Nonpolar solvent for dissolving ester mixtures | Polar solvents for elution | Oil amount (g) | C 16:0 | C 16:1 | C 18:0 (%) | C 18:1 | C 18:2 | C 18:3 (GLA) | Others |
|---|---|---|---|---|---|---|---|---|---|
| n-Hexane (50 g) | Acetone (50 g) | 0.67 | 1.4 | 9.8 | 0.1 | 6.3 | 14.5 | 63.4 | 4.5 |
| n-Hexane (30 g) | Ethyl acetate (30 g) | 0.66 | 2.0 | 9.3 | 0.3 | 8.2 | 12.3 | 66.8 | 1.1 |
| n-Hexane (30 g) | Diethyl ether (30 g) | 0.65 | 2.8 | 8.9 | 1.6 | 5.2 | 10.3 | 69.9 | 1.3 |

EXAMPLE 7

Mucor ambiguus IFO 6472 was subjected to aerobic cultivation just as in Example 1 and the lipid accumulated in the fungus was extracted by such a treatment as homogenization. The lipid obtained in this way was subjected to ester exchange, using 0.2N NaOH ethanol solution, yielding an ethyl ester mixture of the fatty acid composition shown in Table 9.

Five grams of this fatty acid ethyl ester mixture was dissolved in 5 g of n-hexane and this solution was passed through a glass column 1 cm in ID and 15 cm long filled with 5 g of each of various Y type zeolites (24–34 mesh) prepared similarly as in Example 1.

As the elution solvent, 2000 ml of n-hexane only was passed at first. Then 1000 ml of a solution of n-hexane mixed with 0.5% by volume of ethanol was passed. The liquid passing conditions used were the same as of Example 4, but the eluate was divided into 20 ml fractions. The elution solvent of Fraction Nos. 11–13 obtained in this way were removed by distillation, yielding fatty acid ethyl esters. The fatty acid components and their amounts are shown in Table 10.

TABLE 9

| Component | C 16:0 | C 16:1 | C 18:0 | C 18:1 | C 18:2 | C 18:3 (GLA) | Others |
|---|---|---|---|---|---|---|---|
| Composition (%) | 8.8 | 9.2 | 2.8 | 39.4 | 23.5 | 14.3 | 2.0 |

TABLE 10

| Adsorbent | Oil amount (g) | C 16:0 | C 16:1 | C 18:0 (%) | C 18:1 | C 18:2 | C 18:3 (GLA) | Others |
|---|---|---|---|---|---|---|---|---|
| Potassium Y | 0.24 | 0 | 0 | 0.2 | 0.5 | 5.8 | 93.2 | 0.3 |
| Cesium Y | 0.20 | 0 | 0.1 | 0 | 0.1 | 0.2 | 99.4 | 0.2 |
| Rubidium Y | 0.25 | 0 | 0.1 | 0 | 2.2 | 2.4 | 95.1 | 0.2 |
| Ammonium Y | 0.18 | 0.2 | 0.3 | 0.2 | 0.5 | 5.7 | 92.8 | 0.3 |
| Methyl ammonium Y | 0.14 | 0 | 0 | 0 | 0 | 0.5 | 99.2 | 0.3 |
| Dimethyl ammonium Y | 0.12 | 0 | 0.1 | 0 | 0 | 0.2 | 99.5 | 0.2 |
| Ethyl ammonium Y | 0.13 | 0 | 0.1 | 0 | 0.1 | 0.3 | 99.1 | 0.4 |
| Sodium Y | 0.13 | 1.1 | 4.6 | 0.8 | 5.3 | 11.8 | 75.3 | 1.1 |
| Copper Y | 0.06 | 0.5 | 5.2 | 0.2 | 4.1 | 16.2 | 73.2 | 0.6 |

It suggests that in the case of column operation, very high purity GLA ethyl ester can be obtained using Y type zeolites containing either one of cations—$K^+$, $Cs^+$, $Rb^+$, $NH_4^+$, $CH_3NH_2^+$, $(CH_3)_2NH_2^+$ or $C_2H_5NH_3^+$.

What is claimed is:

1. A method of concentrating and separating γ-linolenic acid esters and/or arachidonic acid esters in which their adsorption and desorption are performed in batch operation by bringing in contact with crystalline aluminosilicate zeolites a fatty acid ester mixture containing γ-linolenic acid ester and/or arachidonic acid ester, the method comprising the steps of:

(a) stirring a fatty acid ester mixture containing γ-linolenic acid ester and/or arachidonic acid ester dissolved in a nonpolar solvent and crystalline aluminosilicate zeolites to obtain a fatty acid ester mixture adsorbed by the zeolites, said nonpolar solvent being at least one nonpolar hydrocarbon compound, (b) separating the zeolites which have adsorbed the fatty acid ester mixture, from the nonpolar solvent, and (c) stirring a polar solvent and the zeolites to obtain γ-linolenic acid ester and/or arachidonic ester desorbed from the zeolites, said polar solvent being at least one member selected from the group consisting of alcohols, ketones, halogenated hydrocarbon compounds, ethers and acetate esters.

2. The method of claim 1, wherein the crystalline aluminosilicate zeolites have $SiO_2/Al_2O_2$ molar ratios of 3 or higher.

3. The method of claim 2, wherein the crystalline aluminosilicate zeolites contain at least one member selected from the group consisting of the following cations: $K^+$, $Na^+$, $Rb^+$, $Cs^+$, $Li^+$, $Ca^{2+}$, $Mg^{2+}$, $Ba^{2+}$, $Be^{2+}$, $Sr^{2+}$, $La^{3+}$, $Ce^{3+}$, $Sc^{3+}$, $Y^{3+}$, $Ag^+$, $Cu^{2+}$, $Mn^{2+}$, $Fe^{3+}$, $NH_{4+}$, $CH_3NH_3^+$, $(CH_3)_2NH_2^+$ and $C_2H_5NH_3^+$.

4. The method of claim 3, wherein said crystalline aluminosilicate zeolites are zeolites that have been dried at 120° C.–700° C. after undergoing an ion exchange treatment, when the crystalline aluminosilicate zeolites contain cations other than $Na^+$.

5. The method of claim 4, wherein the said crystalline aluminosilicate zeolites are zeolites that have been dried at 120° C.–250° C. after undergoing an ion exchange treatment, when the crystalline aluminosilicate zeolites contain at least one member selected from the group consisting of $NH_4^+$, $CH_3NH_3^+$, $(CH_3)_2NH_2^+$ and $C_2H_5NH_3^+$.

6. The method of claim 1, wherein the adsorption of the fatty acid ester mixture is made by dissolving the fatty acid ester mixture in a nonpolar solvent in an amount by weight of 30 times or less the amount of the fatty acid ester mixture, adding the crystalline aluminosilicate zeolites in an amount by weight of 0.05–5 times the amount of the fatty acid ester mixture, and stirring this system of 0.5–10 hr.

7. The method of claim 1, wherein the desorption of γ-linolenic acid ester and/or arachidonic acid ester from the zeolites is made by adding the polar solvent in an amount by weight of 0.5–30 times the amount of the crystalline aluminosilicate zeolite, stirring the system for 0.5–5 hr; and repeating these steps 2–5 times.

8. The method of claim 1, wherein the nonpolar hydrocarbon compound is selected from the group consisting of n-heptane, n-hexane, cyclohexane, benzene, p-xylene and n-octane, or a mixture thereof.

9. The method of claim 1, wherein the desorption of γ-linolenic acid ester and/or arachidonic acid ester is made using at least one polar solvent selected from the group consisting of acetone, methanol, ethanol, chloroform, diethyl ether and ethyl acetate.

10. The method of claim 1, wherein the temperature in the absorption step is in the range of 20° C.–50° C.

11. A method of concentrating and separating γ-linolenic acid esters and/or arachidonic acid esters characterized in that their adsorption and desorption are performed in column operation by bringing in contact with crystalline aluminosilicate zeolites a fatty acid ester mixture containing γ-linolenic acid ester and/or arachidonic acid ester, using zeolites containing at least one member selected from the group consisting of the following cations: $K^+$, $Cs^+$, $Rb^+$, $NH_4^+$, $CH_3NH_3^+$, $(CH_3)_2NH_2^+$ and $C_2H_5NH_3^+$ wherein the operation comprises the steps of:
  (a) passing a fatty acid ester mixture containing γ-linolenic acid ester and/or arachidonic acid ester dissolved in a nonpolar solvent through a column filled with said crystalline aluminosilicate zeolites, whereby the fatty acid ester mixture is adsorbed by the zeolites, said nonpolar solvent being at least one nonpolar hydrocarbon compound, and
  (b) passing a polar solvent, or a mixed solvent of a polar solvent and a nonpolar solvent in a ratio of 1–1000:1 by volume, through the crystalline aluminosilicate zeolites to desorb the γ-linolenic acid ester and/or arachidonic acid ester, said polar solvent being at least one member selected from the group consisting of alcohols, ketones, halogenated hydrocarbon compounds, ethers and acetate esters.

12. The method of claim 11, wherein the crystalline aluminosilicate zeolites have $SiO_2/Al_2O_2$ molar ratios of 3 or higher.

13. The method of claim 11, wherein the sodium content by weight of the crystalline aluminosilicate zeolites is 5.0% or lower.

14. The method of claim 11, wherein the aforementioned crystalline aluminosilicate zeolites are dried at a temperature in the range of 120° C.–700° C. after undergoing an ion exchange treatment, when the crystalline aluminosilicate zeolites contain cations other than $Na^+$.

15. The method of claim 14, wherein said crystalline aluminosilicate zeolites are zeolites that have been dried at a temperature in the range of 120° C.–250° C. after undergoing an ion exchange treatment, when the crystalline aluminosilicate zeolites contain at least one member selected from the group consisting of $NH_4^+$, $CH_3NH_3^+$, $(CH_3)_2^+$ and $C_2H_5NH_3^+$.

16. The method of claim 11, wherein the adsorption of the fatty acid ester mixture is made by dissolving the fatty acid ester mixture in the nonpolar solvent in an amount by weight of 30 times or less the amount of the fatty acid ester mixture, and passing this solution through the column filled with the crystalline aluminosilicate zeolites at flow rates of LHSV 0.5–10.

17. The method of claim 11, wherein the desorption of γ-linolenic acid ester and/or arachidonic acid ester is made by passing the polar solvent or the mixed solvent of a polar solvent and a nonpolar solvent through the column at flow rate of LHSV 0.05–10.

18. The method of claim 11, wherein the nonpolar hydrocarbon compound is a member selected from the group consisting of n-heptane, n-hexane, cyclohexane, benzene, p-xylene and n-octane.

19. The method of claim 11, wherein the polar solvent is selected from the group consisting of acetone, methanol, ethanol, chloroform, diethyl ether and ethyl acetate, or a mixture thereof.

20. The method of claim 11, wherein the temperature in the adsorption step is in the range of 20° C.–50° C.

* * * * *